US006451837B1

(12) United States Patent
Baskys

(10) Patent No.: US 6,451,837 B1
(45) Date of Patent: Sep. 17, 2002

(54) NEUROPROTECTIVE EFFECTS OF MITOGEN-ACTIVATED PROTEIN KINASE (MAPK) CASCADE INHIBITORS

(76) Inventor: Andrius Baskys, 10 Cool Brook, Irvine, CA (US) 92612

( * ) Notice: Subject to any disclaimer, the term of this patent is extended or adjusted under 35 U.S.C. 154(b) by 15 days.

(21) Appl. No.: 09/653,065

(22) Filed: Sep. 1, 2000

Related U.S. Application Data

(60) Provisional application No. 60/151,955, filed on Sep. 1, 1999.

(51) Int. Cl.⁷ .......................... A61K 31/40; A01N 43/58
(52) U.S. Cl. .......................... 514/411; 514/33; 514/248; 424/485; 424/486
(58) Field of Search .......................... 514/411, 33, 248; 424/485, 486

(56) References Cited

U.S. PATENT DOCUMENTS

| | | | |
|---|---|---|---|
| 5,446,070 A | 8/1995 | Mantelle | 514/772.6 |
| 5,719,197 A | 2/1998 | Kanios et al. | 514/772.6 |
| 5,830,910 A | 11/1998 | Mattson | 514/411 |
| 5,837,815 A | 11/1998 | Lev et al. | 530/350 |
| 5,945,418 A | 8/1999 | Bemis et al. | 514/248 |
| 5,948,885 A | 9/1999 | Stein et al. | 530/324 |
| 6,037,136 A | 3/2000 | Beach et al. | 435/7.4 |
| 6,074,862 A | 6/2000 | Stein et al. | 435/194 |
| 6,080,557 A | 6/2000 | Sims et al. | 435/69.1 |
| 6,093,742 A | 7/2000 | Salituro et al. | 514/596 |

OTHER PUBLICATIONS

Wei et al., "Induction of apoptosis by quercetin: involvement of heat shock protein." Abstract: Cancer Research, 54(18), pp. 4952–4957, 1994.*

Luk'yanchuk et al., "The role of cAMP phosphodiesterase inhibitors in pharmacotherapy of the hypoxic syndrome." Abstract: Eksperimental'naya i Klinicheskaya Farmakologiya, 61(6), pp. 36–38, (Nov.–Dec., 1998).*

Kim et al., "Quercetin, an inhibitor of lactate transport and a hyperthermic snsitizer of HeLa cells." Abstract: Cancer Research, 44(1), pp. 102–106, 1984.*

Abdel–Hamid, K. M. and Tymianski, M. Mechanisms and effects of intracellular calcium buffering on neuronal survival in organotypic hippocampal cultures exposed to anoxia/aglycemia and excitotoxins. J. Neurosci., 17, 3538, 1997.

Adayev T. Estephan R. Meserole S. Mazza B. Yurkow EJ. Banerjee P. Externalization of phosphatidylserine may not be an early signal of apoptosis in neuronal cells, but only the phosphatidylserine–displaying apoptotic cells are phagocytosed by microglia [published erratum appears in J Neurochem Feb. 1999;72(2):886]. Journal of Neurochemistry. 71(5):1854–64, 1998.

(List continued on next page.)

Primary Examiner—Ralph Gitomer
Assistant Examiner—Devesh Khare
(74) Attorney, Agent, or Firm—Cummings & Lockwood LLC

(57) ABSTRACT

A method is provided for therapeutic use of a class of compounds that are effective in protecting nerve cells from deterioration and cell death arising from degenerative disease, trauma or aging and may be used to achieve a similar effect in male and female subjects with minimal adverse side effects. The method comprises administering a therapeutically effective dose of a natural or synthetic bioflavonoid that acts as an MAPK cascade antagonist. Examples of bioflavonoids that may be used in the present method are apigenin and 2-(2'-amino-3' methoxyphenyl)-oxanaphthalen-4-one (PD098059).

11 Claims, 2 Drawing Sheets

OTHER PUBLICATIONS

Alessandrini, A., Namura, S., Moskowitz, M.A., and Bonventre, J.V. MEK1 protein kinase inhibition protects against damage resulting from focal cerebral ischemia. PNAS. 96, 12866, 1999.

Alessi, D.R., Cuenda, A., Cohen, P., Dudley, D.T., and Saltiel, A.R. PD 098059 is a specific inhibitor of the activation of mitogen–activated protein kinase in vitro and in vivo. The Journal of Biological Chemistry. 270, 27489, 1995.

Cardell M. and Wieloch T. Time course of the translocation and inhibition of protein kinase C during complete cerebral ischemia in the rat. J. Neurochem., 61,1308, 1993.

Choi, D. W. and Rothman, S. M., The role of glutamate neurotoxicity in hypoxic ischemic neuronal death, Annu. Rev. Neurosci., 13, 171, 1990.

Cobb, M.H. and Goldsmith, E.J. How MAP kinases are regulated. The American Society for Biochemistry and Molecular Biology, Inc. 270, 14843, 1995.

Coyle, J. T and Puttfarken P. Oxidative stress, glutamate, and neurodegenerative disorders. Science, 262, 689, 1993.

Deacon E. M., Pongracz J., Griffiths, G. and Lord J. M. Isoenzymes of protein kinase C: differential involvement in apoptosis and pathogenesis. Molec. Pathol., 50, 124, 1997.

English J.D. and Sweatt J.D. A requirement for the mitogen–activated protein kinase cascade in hippocampal long–term potentiation. J. Biol. Chem., 272, 19103, 1997.

Favaron M., Manev H., Siman R., Bertolino M., Szekely A.M., De–Erausquin G., Guidoti A. and Costa E. Down–regulation of protein kinase C protects cerebellar granule neurons in primary culture from glutamate– induced neuronal death. PNAS USA, 87, 1983, 1990.

Fiore R.S., Murphy T.H., Sanghera J.S., Pelech S.L. and Barban J.M. Activation of p42 mitogen–activated protein kinase by glutamate receptor stimulation in rat primary cortical cultures. J. Neurochem., 61, 1626, 1993.

Fukunaga, K. and Miyamoto, E. Role of MAP kinase in neurons. Molecular Neurobiology, 16: (1), 79, 1998.

Gahwiller B. H. Organotypic slice cultures: a technique has come of age. TINS, 11, 484, 1988.

Hwang, D. and Rhee, S.H. Receptor–mediated signaling pathways: potential targets of modulation by dietary fatty acids 1–4. Am. J. Clin. Nutr. 70, 545, 1999.

Ikeda , M., Kito, H and Sumpio, E. Phosphatidylinositol–3 Kinase Dependent MAP Kinase Activation via p21ras in Endothelial Cells Exposed to Cyclic Strain. Biochemical and Biophysical Research Communications, 257, 668, 1999.

Islam N, Aftabuddin M., Moriwaki A and Hori Y. Immunocytochemical distribution of gamma isoform of protein kinase C (PKC–gamma) following incomplete ischemia. Indian J. Physiol. Pharmacol., 39, 37, 1995.

Kharlamov A., Guidoti A., Costa E., Hayes R. and Armstrong D. Semisynthetic sphingolipids prevent protein kinase C translocation and neuronal damage in the perifocal area following a photochemically induced trombotic brain cortical lesion. J. Neurosci., 13, 2483, 1993.

Kitagawa, H., Warita, H., Sasaki, C., Ri Zhang, W., Sakai, K., Shiro, Y., Mitsumoto, Y., Mori, T., and Abe, K. Immunoreactive Akt, Pi3–K and ERK protein kinase expression in ischemic rat brain. Neuroscience Letters, 274, 45, 1999.

Koh J. Y., Palmer E. and Cotman C. W. Activation of metabotropic glutamate receptors attenuates N–methyl–D–aspartate neurotoxicity in cortical cultures. PNAS USA, 88, 9431, 1991.

Kurino M., Fukunaga K., Ushio Y. and Miyamoto E. Activation of mitogen–activated protein kinase in cultured rat hippocampal neurons by stimulation of glutamate receptors. J. Neurochem., 65, 1282, 1995.

Lin W.W., Wang C.W. and Chuang D.M. Effects of depolarization and NMDA antagonists on the role of survival of cerebrellar granule cells: a pivotal role for protein kinase C isoforms. J. Neurochem., 68, 2577, 1997.

Mattson M. P. Evidence for the involvement of protein kinase C in neurodegenerative changes in cultured human cortical neurons. Exp. Neurol., 112, 95, 1991.

Mattson et al. Roles of nuclear factor KB in neuronal survival and plasticity, J. Neuronchem. 74, 443–456 (2000).

Miettinen S., Roivainen R., Hokfelt T. and Koistinahol J. Specific induction of protein kinase C–delta subspecies after transient middle cerebral artery occlusion in the rat brain: inhibition by MK–801. J. Neurosci., 16, 6236, 1996.

Namura, S., Alessandrini, A., Bonventre, J.V., and Moskovwitz, A. Inhibition of MEK1/ERK pathway reduces brain damage following focal cerebral ischemia and reperfusion in mice (Abstract), 23rd International Joint Conference on Stroke and Cerebral Circulation (1998).

Nares M., Kuluz J., Neary J., Kang Y., Xu E. and Schleien C.L. Mitogen–activated protein (MAP) kinase activity during and after transient focal cerebral ischemia in rats. Soc. Neurosci. Abs., 24 Pt. 1), 223, 1998.

Newell D. W., Barth A., Papermaster V. and Malouf A. T. Glutamate and non–glutamate receptor mediated toxicity caused by oxygen and glucose deprivation in organotypic hippocampal cultures. J. Neurosci., 15, 7702, 1995.

Newton A.C. Protein kinase C: structure, function and regulation. J. Biol. Chem., 270, 28495, 1995.

Ozawa, H., Shioda, S, Dohi, K., Matsumoto, H., Mizushima, H., Zhou, Ji Zhou, Ch., Funahashi, H., Nakai, Y., Nakajo, S., and Matsumoto, K. Delayed neuronal cell death in the rat hippocampus is mediated by the mitogen–activated protein kinase signal transduction pathway. Neuroscience Letters 262, 57, 1999.

Park, J.A., Koh, J.Y. Induction of an immediate early gene egr–1 by zinc through extracellular signal–regulated kinase activation in cortical culture: its role in zinc–induced neuronal death. Journal of Neurochemistry, 73(2), 450, 1999.

Roisin M.P., Leinekugel X. and Tremblay E. Implication of protein kinase C in mechanisms of potassium– induced long–term potentiation in rat hippocampal slices. Brain Res., 745, 222, 1997.

Runden E., Seglen P.O., Haug F.–M., Ottersen O.P., Wieloch T., Shamloo M. and Laake J.H. Regional selective neuronal degeneration after protein phosphatase inhibition in hippocampal slice cultures: evidence for a MAP kinase–dependent mechanism. J. Neurosci., 18, 7296, 1998.

Sakai N., Sasaki K., Ikegaki N., Shirai Y., Ono Y . and Saito N. Direct visualization of the translocation of the gamma–PKC in living cells using fusion proteins with green fluorescent protein. J. Cell. Biol., 139, 1465, 1997.

Sato N., Kamino K., Tateishi K., Satoh T., Nishiwaki Y., Yoshiwa A., Miki T. and Ogihara T. Elevated amyloid beta protein (1–40) level induces CREB phosphorylation at serine 133 via p44/42 MAP kinase (Erk1/2)– dependent pathway in rat pheochromocytoma PC12 cells. Biochem. Piophys. Res. Com.,232, 637, 1997.

Shioda, S., Ozawa, H., Dohi, K., Mizushima, H., Matsumoto, K., Nakajo, S., Takaki, A., Zhou, C.J., Nakai, Y., and Arimura, A. PACAP protects hippocampal neurons against apoptosis: involvement of JNK/SAPK signaling pathway. VIP, PACAP, and Related Peptides, 865, 111, 1998.

Soler, R., Egea, J., Mintenig, G., Sanz–Rodriguez, C. Iglesias, M. and Comella, J. Calmodulin is involved in membrane depolarization–mediated survival of motoneurons by phosphatidylinositol–3 kinase– and MAPK–independent pathways. J. Neurosci., 18(4), 1230, 1998.

Stoppini L., Buchs P.A. and Muller D. A simple method for organotypic cultures of nervous tissue. J. Neurosci. Meth., 37, 173, 1991.

Tong L., Toliver–Kinsky T., Taglialatela G., Werrbach–Perez K., Wood T. and Perez–Polo R. Signal transduction in neuronal death. J. Neurochem., 71, 447, 1998.

Vornov J. J., Tasker, R. C. and Coyle T. J. Delayed protection by MK–801 and tetrodotoxin in a rat organotypic hippocampal culture model of ischemia. Stroke, 25, 457, 1994.

Xia Z., Dickens M., Raingeuad J., Davis R.J. and Greenberg M.E. Opposing effects of ERK and JNK–p38 MAP kinases on apoptosis. Science, 270, 1326, 1995.

Xia Z., Dudek H., Miranti C.K. and Greenberg M.E. Calcium influx via the NMDA receptor induces immediate early gene transcription by a MAP kinase/ERK–dependent mechanism. J. Neurosci., 16, 5425, 1996.

Zablocka B and Domanska–Janik K. Involvement of protein kinase C in various cellular systems transducting ischemia evoked signal. Acta Neurobiol. Exp., 53, 25, 1993.

\* cited by examiner

NEUROPROTECTIVE EFFECTS OF MITOGEN-ACTIVATED PROTEIN KINASE (MAPK) CASCADE INHIBITORS

This application claims the benefit of U.S. Provisional Application No. 60/151,955 filed on Sep. 1, 1999.

FIELD OF THE INVENTION

The present invention relates to a method of treatment to achieve neuroprotection of cells in the central nervous system from death and for stimulating nerve cell survival in subjects with neurodegenerative disorders.

BACKGROUND OF THE INVENTION

Pathological conditions resulting from the accelerated or ongoing death of nerve cells in the central nervous system are prevalent in today's society and include acute or chronic neurodegenerative disorders. An example of a chronic neurodegenerative disorder is Alzheimer's disease. Other examples of neurodegenerative disorders include Parkinson's disease; Huntington's disease; AIDS Dementia; Wernicke-Korsakoff's related dementia (alcohol induced dementia); age related dementia; age associated memory impairment; brain cell loss due to head trauma, stroke, hypoglycemia, ischemia, anoxia, hypoxia, cerebral edema, arteriosclerosis, hematoma or epilepsy; spinal cord cell loss due to any of the conditions listed under brain cell loss; and peripheral neuropathy. Chronic and acute neurodegenerative diseases and acute nerve cell injury, as well as associated mortality and morbidity, have been largely untreatable with previous methods. Patient disability resulting from these conditions can cause a significant reduction in quality of life. In addition, these conditions impose a high cost to the patient and to society for long term care. Accordingly, effective therapeutic approaches directed to the prevention or reduction of nerve cell death or nerve cell damage associated with neurodegenerative diseases and acute nerve cell injury are needed. Specifically, an efficacious method for treating conditions in the brain resulting from neuron loss is needed that is relatively non-toxic, suitable for use in both females and males, and which can readily access the brain across the blood-brain barrier. The terms "nerve cells" and "neurons" are used interchangeably herein to refer to cells in the central nervous system, including the brain.

1. The Mechanism of Neuron Damage

The amino acids glutamate and aspartate are known to function as excitatory neurotransmitters in the mammalian central nervous system. These amino acids activate a large series of excitatory neurotransmitter receptors known as "glutamate receptors". These glutamate receptors, along with the various neurotransmitters which activate them, make up the "glutamatergic system", the dominant excitatory nerve impulse transmission system of the mammalian central nervous system. A detailed explanation of the functioning of the glutamatergic system can be found in Olney, et al., U.S. Pat. No. 5,902,815.

Over the last few years, it has come to be recognized that overstimulation of excitatory neurotransmitter receptors can have serious pathological consequences for nerve cells. The overstimulation of cultured nerve cells in vitro by glutamate, for example, can lead to nerve cell death. Nerve cell death caused by such overstimulation is referred to as "excitotoxicity." Excitotoxicity is thought to be important in the pathogenesis of several neurodegenerative disorders, including stroke and ischemic injury. Excitotoxicity has been studied in vivo and in vitro, including in organotypic hippocampal explant preparations. Excitotoxicity is caused by $Ca^{2+}$ overload resulting from its influx through highly $Ca^{2+}$-permeable glutamate receptors sensitive to N-methyl-D-aspartate ("NMDA") receptors and the resulting activation of intracellular kinases. One of the first events associated with excitotoxicity and nerve cell death is activation of protein kinase C ("PKC"). It has been shown that inhibition or reduction of PKC formation protects against nerve cell death following ischemia.

PKC refers to a family of more than ten $Ca^{2+}$/phospholipid-dependent and independent threonine-serine kinase isozymes which regulate a multitude of mechanisms including cell differentiation and response to injury. PKC is abundant in neurons. It has been established that ischemia affects PKC activity and distribution. Ischemic nerve cell death has been associated with induction of PKC-delta isozyme. This effect can be blocked by NMDA inhibitors. Increased PKC-gamma immunoreactivity following incomplete ischemia has been found in the hippocampus. It has been shown that NMDA receptor stimulation can trigger PKC-gamma and beta isozyme activation. Protection of cultures by the NMDA antagonist MK-801 (dizocilpine maleate) has been associated with increases in PKC gamma, lambda, iota and micron isozymes, and PKC epsilon. PKC alpha, $beta_1$, $beta_2$ remained unchanged suggesting that PKC isozymes can play a significant role in regulating cell death. These data are consistent with the view that inhibition of PKC can confer neuroprotection.

2. The MAPK Cascade

Several PKC isozymes (for example, PKC-delta and epsilon) activate the mitogen-activated protein kinase (MAPK) cascade. The MAPK family consists of key regulatory proteins that are known to regulate cellular responses to both proliferative and stress signals. MAPK is abundantly expressed in nerve cells and may be necessary for cellular commitment to apoptosis. Apoptosis, also know as "programmed cell death", is a mechanism of nerve cell death initiated by activation of intracellular enzymes known as caspases. When a cell is undergoing the apoptotic process, its membrane disintegrates which exposes the inside of the membrane's lipid bilayer. This process is sometimes referred to as the "phosphatidylserine flip-flop."

It is believed that nerve cells will enter apoptosis if they are stimulated with a mitogenic agent, forcing them to divide. Nerve cells normally cannot divide, and if forced to divide, they instead enter the apoptosis program and die. Nerve cells may enter the division cycle when the MAPK cascade is activated. Accordingly, blocking the MAPK cascade can protect nerve cells from death.

MAPKs consist of several enzymes, including a subfamily of extracellular signal-activated kinases (ERK1 and ERK2) and stress-activated MAPKs. There are three distinct groups of MAPKs in mammalian cells: a) extracellular signal-regulated kinases (ERKs), b) c-Jun N-terminal kinases (JNKs) and c) stress activated protein kinases (SAPKs). As used herein, the term "MAPK cascade" refers to those protein kinases or protein kinase cascades located within nerve cells that are inhibited by 2-(2'amino-3' methoxphenyll)-oxanaphthalen-4-one(referred to herein" PD098059), apigenin, or other similar bioflavonoids and which, upon activation, activate various transcription factors. Other as yet uncharacterized protein kinases which are similarly inhibited by PD098059 or apigenin and which are located within nerve cells, and which, upon activation, activate various transcription factors, are also within the scope of the term "MAPK cascade".

An example of the MAPK cascade can be described as follows. PKC activation or other factors (e.g. increases in free intracellular $Ca^{2+}$) activates small proteins called Ras/Raf-1, which in turn activate MAPK/ERK kinases referred to as MEKs. The MEKS in turn activate ERKs. The ERKS translocate to the cell nucleus where they activate transcription factors and thereby regulate cell proliferation. The inhibition of these protein kinases produces neuroprotective and neuron-treating effects as does the inhibition of the MAPK cascade. Examples of such kinases are mitogen-activated protein kinase 1 and 2, their homologues and isoforms, extracellular signal-regulated kinases (ERKs) their homologues and isoforms (ERK1, ERK2, ERK3, ERK4), and a group of kinases known as MAP/ERK kinases 1 and 2 or MEK1/2.

Exposure of cells to stress activates protein kinases by a variety of mechanisms. For example, ischemia, NMDA and amyloid peptides activate MAPK. Studies of functional roles of MAPKs in nerve tissue suggest that MAPK could be an important regulator of nerve cell death and plasticity. Thus, MAPK activation is required for hippocampal long-term potentiation (LTP). Okadaic acid, an inhibitor of protein phosphatase 2A, which dephosphorylates MEK1/2 and thus enhances and prolongs its activity, increased nerve cell death in cultured hippocampal slices. The experiments described in this application revealed that substances which are inhibitors of the MAPK cascade are neuroprotective.

3. β-Amyloid Protein Inhibition

Alzheimer's Disease (AD) is a progressive neurodegenerative disease which is histologically characterized by an accumulation of neuritic plaques and neurofibrillary tangles and by neuron death. A major component of these neuritic plaques is the β-protein, which is derived from a precursor protein called the β-amyloid precursor protein (APP). The β-amyloid protein itself has been shown to be toxic to neurons in vitro.

The β-amyloid protein has, moreover, also been shown to potentiate the excitotoxicity caused by the overstimulation of glutamate receptors. When mature neuron cultures are exposed to doses of β-amyloid that are too low to cause neuron degeneration by themselves and are then subsequently exposed to sublethal doses of glutamate, massive neuron death occurs. In addition to potentiating the toxicity of glutamate, β-amyloid has been shown to increase the toxicity to neurons of exposure to NMDA and kainate, which are agonists of specific glutamate receptors. There is also evidence that β-amyloid exposure specifically makes neurons more susceptible to injury or death. The present invention provides a method to block this effect of β-amyloid by administering MAPK cascade inhibitors, thereby protecting neurons from death.

4. Propidium Iodide Assay

As described in detail herein, experiments demonstrating the neuroprotective properties of the bioflavonoids have been conducted using propidium iodide assays. Propidium iodide is a nuclear stain that binds RNA or DNA with little or no base pair preference. It can be excited by argon laser (488–547 nm), and the resulting emission can be collected in the red wavelengths of the spectrum. Propidium iodide is excluded from neurons that retain membrane integrity which makes it a useful and widely used marker of cell death. Recent studies show that, in severely apoptotic neurons, membrane permeabilisation occurs and they become stained by propidium iodide. This is the same stage of apoptosis when DNA laddering and phosphatidylserine flip-flops occur, and activity of caspases is high. Propidium iodide does not distinguish between apoptosis and necrosis.

As described above, at least two intracellular kinase systems may be involved in regulation of nerve cell death regardless of the initial mechanism of their activation. Therapeutic agents that are selected on the basis of their capability to inhibit these kinase systems may have generalized utility in treating nerve cell loss caused by disease or trauma in patients. Accordingly, it is an object of the present invention to provide a method for administering a class of compounds that have demonstrated biological efficacy in protecting neurons from cell death, where such compounds could be used in the treatment of the chronic as well as the acute conditions caused by neurodegenerative diseases, trauma, and aging at non-toxic dosages.

SUMMARY OF THE INVENTION

The present invention provides a method for protecting nerve cells from deterioration and cell death arising from disease, trauma or aging and may be used to achieve a similar effect in male and female subjects with minimal adverse side effects.

One aspect of the present invention involves a method of treating nervous system cells by administering a therapeutically effective dose of a MAPK cascade antagonist which is effective in preventing or treating damage to nerve cells caused by exposure of the cells to NMDA. The cells can be mammalian nervous system cells, and the cells can be treated in vivo. Alternatively, the nervous system cells can be treated in vitro. MAPK cascade antagonists useful in treating cells of the nervous system include, for example, PD098059 and apigenin, or pharmaceutically acceptable salts of these compounds.

Another aspect of the present invention involves a method of treating nervous system cells by administering a therapeutically effective dose of a MAPK cascade antagonist which is effective in preventing or treating damage to the nerve cells caused by the withdrawal of growth factors from the culture medium. The cells can be mammalian nervous system cells, and the cells can be treated in vivo. Alternatively, the nervous system cells can be treated in vitro. MAPK cascade antagonists useful in treating cells of the nervous system include, for example, PD098059 and apigenin, or pharmaceutically acceptable salts of these compounds.

BRIEF DESCRIPTION OF THE DRAWINGS

So that those having ordinary skill in the art to which the subject invention appertains will more readily understand how to perform the method of the subject invention, reference may be had to the drawings wherein.

DETAILED DESCRIPTION OF THE PREFERRED EMBODIMENTS

Figure 1:
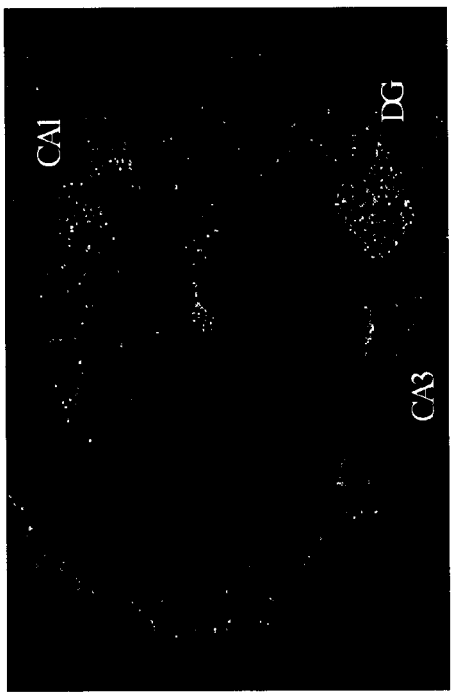
FIG. 1 is a photograph depicting the results of an experiment in which propidium iodide fluorescence, appearing as bright dots in the photograph, was measured in cultured hippocampal tissue explants exposed to NMDA alone. Increased intensity of the fluorescence shows an increased degree of nerve cell death.

"Neuroprotection" is defined here and in the claims as the inhibition of progressive deterioration of neurons that leads to nerve cell death.

"Neurodegenerative disorder" is defined here and in the claims as a disorder in which progressive loss of neurons occurs either in the peripheral nervous system or in the central nervous system. Examples of neurodegenerative disorders include: chronic neurodegenerative diseases such as Alzheimer's disease, Parkinson's disease, Huntington's chorea, diabetic peripheral neuropathy, multiple sclerosis, amyotrophic lateral sclerosis; aging; and acute neurodegenerative disorders including: stroke, traumatic brain injury, schizophrenia, peripheral nerve damage, hypoglycemia, spinal cord injury, epilepsy, and anoxia and hypoxia. These examples are not meant to be comprehensive or limiting in any way but serve merely as an illustration of the term "neurodegenerative disorder."

The present invention is directed to a novel method that inhibits nerve cell death caused by activation of intracellular enzymes that can cause nerve cell death. For example, the present method inhibits nerve cell death caused by the intracellular enzymes known as the MAPK cascade. The method is used for treating and preventing nerve cell death caused by acute or chronic neurodegenerative disorders. The method comprises supplying at least one bioflavonoid that acts as an inhibitor of intracellular enzymes, such as MAPK, that, when activated, cause nerve cell damage and death, and administering a therapeutically effective dose of the bioflavonoid to an animal or human. The class of neuroprotective compounds that may be used in the present method include (a) compounds that can be extracted from plants, for example apigenin, or (b) synthetic compounds of a similar composition, for example 2-(2'-amino-3'methoxyphenyl)-oxanaphthalen-4-one. The bioflavonoid may be administered orally, intramuscularly, transdermally, buccally, intravenously or subcutaneously. Also, the bioflavonoid may be administered by dose or by controlled release vehicles. Pharmaceutically acceptable salts of the compounds may also be used.

In one embodiment of the invention, the bioflavonoid 2-(2'-amino-3'methoxyphenyl)-oxanaphthalen-4-one (referred to herein as "PD098059") is administered as an intracellular enzyme inhibitor. The PD098059 is administered to achieve a blood plasma concentration of PD098059 of up to 100 $\mu$M, with a plasma concentration preferably between about 30 $\mu$M and about 90 $\mu$M. As described in Example 1 below, this level of PD098059 has been shown to be effective in providing neuroprotection to nerve cells in the presence of intracellular enzymes that can cause neuron cell death.

In another embodiment of the invention, the bioflavonoid apigenin is administered as the enzyme inhibitor. The apigenin is administered to achieve a blood plasma concentration of up to 100 $\mu$M, with a plasma concentration preferably between about 25 $\mu$M and 100 $\mu$M. As described in Example 1 below, this level of apigenin has been shown to be effective in providing neuroprotection to nerve cells in the presence of intracellular enzymes.

As will be apparent to one skilled in the art from the disclosure herein, other bioflavonoids, or pharmaceutically acceptable salts of the bioflavonoids, may be used in the present method to achieve neuroprotection. Specific examples of compounds that may be used in the method of the present invention are apigetrin, apiin, pelargidenon, versulin, cossmetiin, apioside, cosmosiin, cosmosiine cosmosioside, baicalin, cirsimaritin, 6-hydroxyluteolin, luteolin, plantaginin, rhoifolin, sorbavin, afrelin, hyperin, isoquercitrin, isorhamnetin, kaempferitrin, kaempferol-7-glucoside, oxyayanin-A, quercetin, quercitrin, rhamnetin and rutin. Furthermore, any of these compounds may be supplied in the form of a prodrug that may be metabolized to form an active MAPK cascade antagonist. Administration of any of the compounds of the invention may include the use of a single compound or a mixture of neuroprotective compounds.

The neuroprotective compounds used in the present invention can be administered in pharmaceutical compositions. The recommended route of administration of the neuroprotective compound includes oral, intramuscular, transdermal, buccal, intravenous and subcutaneous. Methods of administering the compound of the invention may be by dose or by controlled release vehicles.

The pharmaceutical compositions may be in the form of tablets, dragees, capsules, pills, solutions, suspensions, emulsions or ophthalmic preparations or any other appropriate form for delivery of pharmaceutical compositions. The pharmaceutical compositions in solid form may contain non-aqueous diluents, including for example fillers and extenders, binding agents, moisturizing agents, disintegrating agents, surface active agents, adsorptive carriers, lubricants or any other appropriate diluent known to one skilled in the art. Pharmaceutical compositions in liquid form may contain liquid diluents such as, for example, water, ethyl alcohol, propylene glycol or any other appropriate diluent known to one skilled in the art. For parenteral administrations, solutions and suspensions should be sterile and, if appropriate, blood-isotonic.

As used herein, the term "therapeutically effective dose" means a dose of a MAPK cascade inhibitor which will treat or protect a subject from acute or chronic neurodegenerative disorders such as for example Alzheimer's disease. Therapeutically effective doses of the MAPK cascade inhibitor can be determined according to standard medical principles under the direction of a physician or veterinarian.

As described in detail in Examples 1–3 below, assays have been conducted demonstrating the neuroprotective effects that are achieved by the method of the present invention.

Assays to Demonstrate Neuroprotective Compounds

EXAMPLE 1

The efficacy of the method of the present invention has been demonstrated in experiments conducted on cultured hippocampal tissue explants prepared according to the method of Stopini et al. (Stoppini L., Buchs P. A. and Muller D. A simple method for organotypic cultures of nervous tissue. J. Neurosci. Meth., 37, 173, 1991). Seven day old Wistar rat pups were anaesthetized with fluothane, decapitated and transverse hippocampal slices (400 microns) were cultured for 12 days on 6-well tissue culture plates containing 1 ml of culture medium. The medium composition was 50% minimal essential medium (MEM), 25% horse serum, 25% Earl's balanced salt solution with D-glucose and HEPES, penicillin G and streptomycin sulfate, 5000 units/ml and 5 $\mu$g/ml respectively and the pH, 7.15. Slices were cultured at 36.5° C., 100% humidity, 95% air and 5% CO2 atmosphere, and were fed twice weekly by 50% medium exchange. All drugs were dissolved in water or dimethyl-sulfoxide (DMSO, final concentration was 0.1%) to make stock solutions. Controls for DMSO effects were performed where appropriate. To apply a drug, the stock solution was dissolved in 1 ml of fresh culture medium to make a desired concentration. Then, hippocampal slices were transferred for a specified time interval to the fresh medium containing the drug. To terminate the drug action, slices were again transferred to a fresh medium containing 2 mg/ml propidium iodide (PI). The medium temperature was kept at 36° C. during the transfers. Since the change of medium induced nerve cell death, control experiments were performed by transferring hippocampal slices an equal number of times into the fresh medium with the intervals between transfers equal to the time interval that slices were exposed to the drug. In a separate series of experiments the medium replacement was performed twice with a 30 minute interval in order to induce cell death. Cell death was measured as the PI fluorescence intensity by using MRC-600 Laser Scanning Confocal Imaging System. PI was added to the medium 30 minutes prior to taking control images (immediately before the drug treatment). Images were taken immediately before and 24 hours after the drug treatment or, where cell death was induced by the fresh medium, 24 and 72 hours after the last medium exchange. Each experiment was performed at least in triplicate, on 5–6 slices each time and data expressed as an average of all experiments. Cell death index was derived from PI fluorescence intensity normalized to the intensity values obtained after the 48 hour exposure of slices to an ambient temperature of 4° C. Image analysis was performed off-line using ScionImage (Scion Corporation) image analysis software. Differences were considered significant where $p<0.05$ (unpaired two-tailed t-test).

As illustrated in FIG. 1, exposure of hippocampal slices to N-methyl-D-aspartate (NMDA) (2.5–500 $\mu$M) for 30 minutes resulted in marked cell death in the CA1–CA4 region of the hippocampus. The effect was concentration-dependent and could be blocked by the NMDA receptor antagonist d-APV but not the Na+ channel blocker tetrodotoxin or non-NMDA receptor antagonists. These data suggest that cell death was mediated by NMDA receptors and was not dependent on neurotransmitter release. Assuming that exposure of slices to a temperature of 4° C. killed 100% of cells, 50 $\mu$M of NMDA killed approximately 30% of all cells and this concentration of NMDA (and the corresponding level of death) was used as a reference point in all further experiments. In another region of the hippocampus, the dentate gyrus, NMDA (2.5–500 $\mu$M) did not induce concentration-dependent increase in cell death, which reflects selective vulnerability of the hippocampal neurons.

Figure 2:
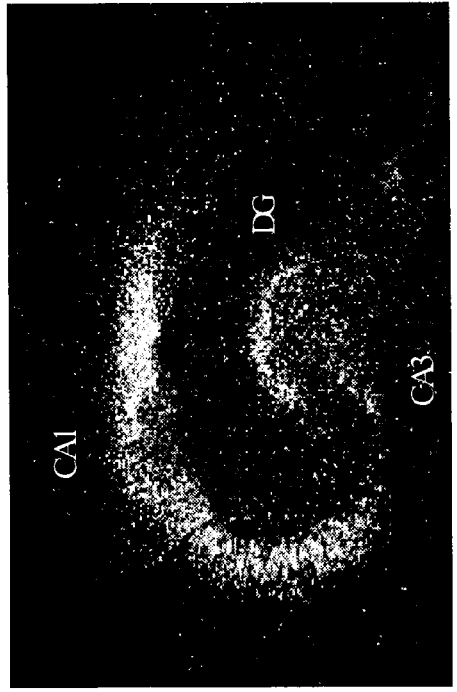
FIG. 2 is a photograph depicting the results of an experiment in which propidium iodide fluorescence, appearing as bright dots in the photograph, was measured in cultured hippocampal tissue explants exposed to NMDA in combination with PD098059. Increased intensity of the fluorescence shows an increased degree of nerve cell death.
Figure 3:
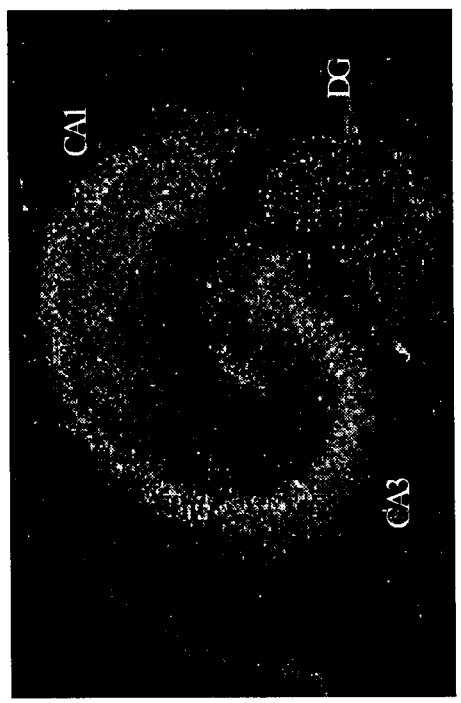
FIG. 3 is a photograph depicting the results of an experiment in which propidium iodide fluorescence, appearing as bright dots in the photograph, was measured in cultured hippocampal tissue explants exposed to NMDA in combination with protein kinase C inhibitor staurosporine. Increased intensity of the fluorescence shows an increased degree of nerve cell death.
Figure 4:
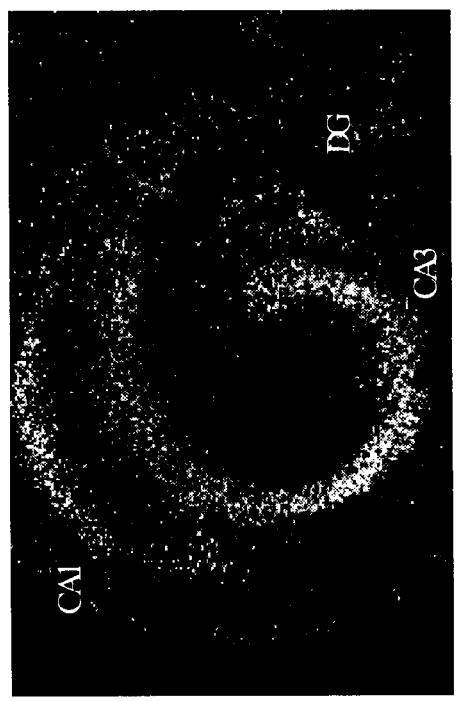
FIG. 4 is a photograph depicting the results of an experiment in which propidium iodide fluorescence, appearing as bright dots in the photograph, was measured in cultured hippocampal tissue explants exposed to NMDA in combination with PI-3K inhibitor wortmannin. Increased intensity of the fluorescence shows an increased degree of cell death.

To show that MAPK inhibitors are effective in reducing nerve cell death, hippocampal slices were treated for 2 hours with the MAPK cascade inhibitors PD098059 (30–90 $\mu$M) or apigenin (25–100 $\mu$M) prior to application of excitotoxin N-methyl-D-aspartate (NMDA, 50 $\mu$M). As shown in FIG. 2, PD098059 significantly reduced NMDA toxicity. The reduction of fluorescence intensity as compared to FIG. 1 illustrates the neuroprotective effect of PD098059. PD098059 was also effective in reducing NMDA-induced cell death when applied immediately after NMDA, suggesting that this neuroprotective action was unlikely due to NMDA receptor/channel blockade but is attributed to MAPK inhibition. In contrast, as shown in FIG. 4, wortmannin (1–5 $\mu$M) an inhibitor of another intracellular kinase, phosphoinositol-3 kinase (PI-3K), did not reduce NMDA toxicity. This demonstrates that the inhibitor must specifically inhibit the MAPK cascade to impart the neuroprotective effects of the present invention. As shown in FIG. 3, the PKC inhibitor staurosporine, which indirectly blocks MAPK activation was also somewhat effective in protective nerve cells against NMDA toxicity. However, staurosporine was clearly not as effective as the direct MAPK inhibitor PD098059.

Figure 5:
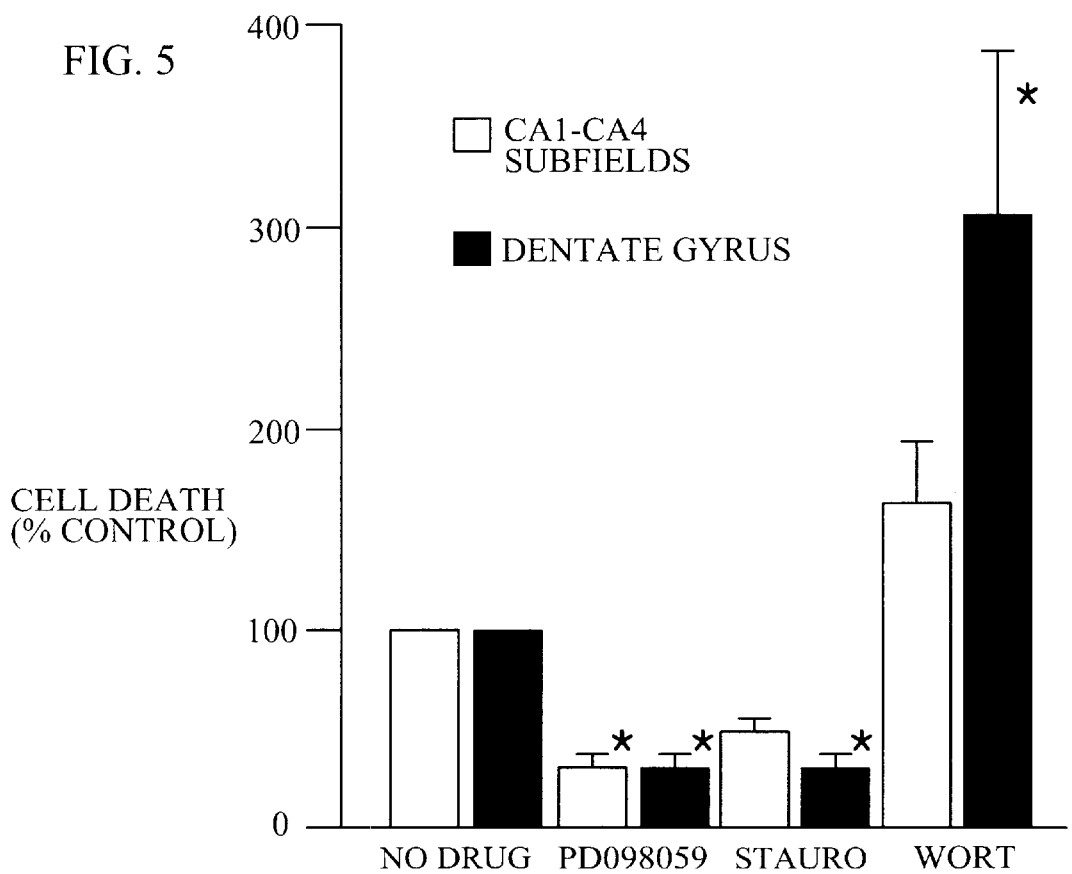
FIG. 5 is a graph showing the results of the experiments described in Example 1, demonstrating the neuroprotective effects of PD098059.

The neuroprotective activity of the MAPK cascade inhibitor PD098059 in comparison to the other compounds tested is summarized in the graph in FIG. 5. As shown in FIG. 5, at 24 hours after NMDA exposure, the number of dead cells in hippocampal explants is 45% lower in the presence of 0.2 $\mu$M of staurosporine. The number of dead cells in explants treated with PD098059 was 95% lower than in explants treated with NMDA alone, and 33% lower than in explants treated with staurosporine. Wortmannin did not exhibit any significant reduction in nerve cell death was without any effect.

EXAMPLE 2

Figure 6:
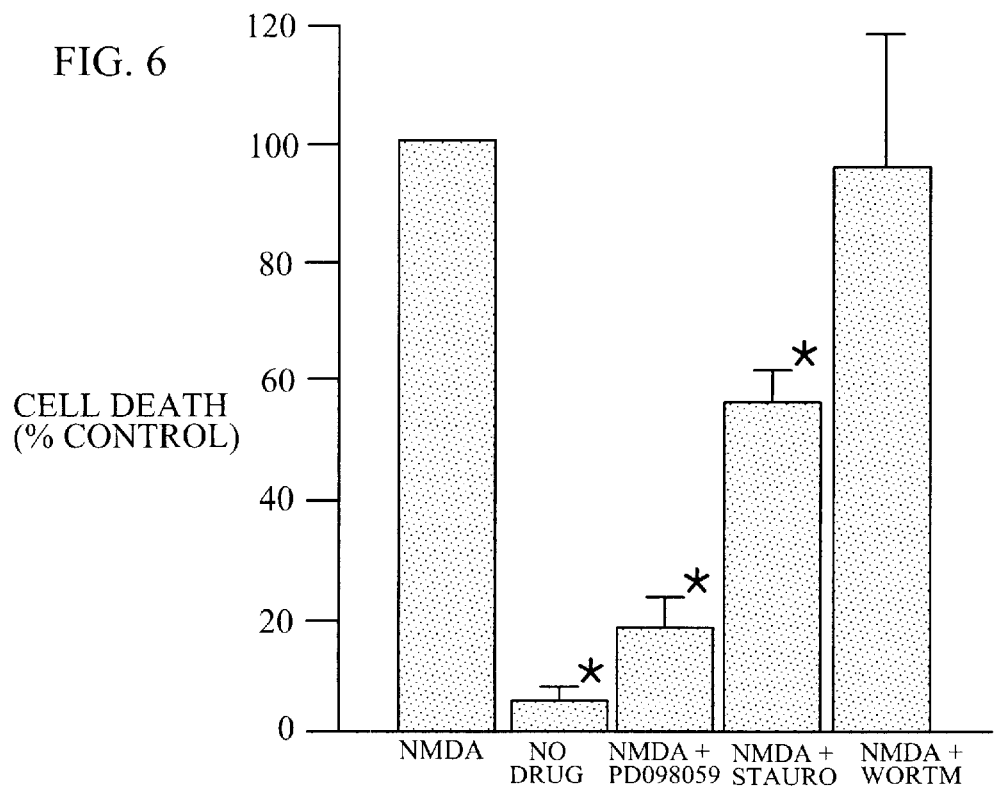
FIG. 6 is a graph showing the results of the experiments described in Example 2, demonstrating the neuroprotective effects of PD098059.

In another example of the method of the present invention, cell death was induced by diluting the culture medium with freshly prepared culture medium. There was a significant increase in cell death in slices subjected to transfers to a fresh medium at 24 and 72 hours after the first transfer, in comparison to cultures that received no transfers. The increase occurred in both CA1–CA4 and dentate gyrus areas and was not blocked by NMDA receptor antagonist AP5 (20 $\mu$M) suggesting that this was not an NMDA-dependent process. As shown in FIG. 6, addition of PD098059 (30–90 $\mu$M) for 2 hours prior to the exposure of cultures to the fresh medium significantly reduced cell death at 24 hours and at 72 hours. Wortmannin (1 $\mu$M), which inhibits growth factor receptor signaling, significantly enhanced cell death at 24 and 72 hours suggesting that growth factor withdrawal contributed to cell death due to the culture medium exchange.

EXAMPLE 3

In a further example of the method of the present invention, cell death was induced in cultured slices treated with the toxic fragment 25–35 of the amyloid $\beta$-protein. Experiments were performed as in Example 2, with the difference that the culture medium contained small quantities of L-glutamic acid (cultures were healthier in its presence). Toxic $\beta$-amyloid peptides were added to cultured hippocampal tissue explants subjected to 100% culture medium exchange. Amyloid peptides induced cell death in hippocampal slices. However, addition of 30–90 $\mu$M of PD098059 for 2 hours prior to the addition of toxic peptides prevented cell death.

The purpose of the above description and examples is to illustrate some embodiments of the present invention without implying any limitation. As will be recognized by those of skill in the art based on the teachings herein, numerous changes and modifications may be made to the above-described invention without departing from its spirit or scope as defined in the appended claims. Accordingly, this detailed description of preferred embodiments is to be taken in an illustrative, as opposed to a limiting sense. All patents and publications cited in the bibliographic citation below are incorporated by reference in their entireties.

REFERENCES

Abdel-Hamid, K. M. and Tymianski, M. Mechanisms and effects of intracellular calcium buffering on neuronal survival in organotypic hippocampal cultures exposed to anoxia/aglycemia and excitotoxins. J. Neurosci., 17, 3538, 1997.

Adayev T. Estephan R. Meserole S. Mazza B. Yurkow E J. Banerjee P. Externalization of phosphatidylserine may not be an early signal of apoptosis in neuronal cells, but only the phosphatidylserine-displaying apoptotic cells are phagocytosed by microglia [published erratum appears in J Neurochem 1999 Feb;72(2):886]. Journal of Neurochemistry. 71(5):1854–64, 1998

Cardell M. and Wieloch T. Time course of the translocation and inhibition of protein kinase C during complete cerebral ischemia in the rat. J. Neurochem., 61,1308, 1993.

Choi, D. W. and Rothman, S. M., The role of glutamate neurotoxicity in hypoxiic ischemic neuronal death, Annu. Rev. Neurosci., 13, 171, 1990.

Coyle J. T and Puttfarken P. Oxidative stress, glutamate, and neurodegenerative disorders. Science, 262, 689, 1993.

Deacon E. M., Pongracz J., Griffiths G. and Lord J. M. Isoenzymes of protein kinase C: differential involvement in apoptosis and pathogenesis. Molec. Pathol., 50, 124, 1997.

English J. D. and Sweatt J. D. A requirement for the mitogen-activated protein kinase cascade in hippocampal long-term potentiation. J. Biol. Chem., 272, 19103, 1997.

Favaron M., Manev H., Siman R., Bertolino M., Szekely A. M., De-Erausquin G., Guidoti A. and Costa E. Down-regulation of protein kinase C protects cerebellar granule neurons in primary culture from glutamate-induced neuronal death. PNAS USA, 87, 1983, 1990.

Fiore R. S., Murphy T. H., Sanghera J. S., Pelech S. L. and Baraban J. M. Activation of p42 mitogen-activated protein kinase by glutamate receptor stimulation in rat primary cortical cultures. J. Neurochem., 61, 1626, 1993.

Gahwiller B. H. Organotypic cultures of neural tissue. TINS, 11, 484, 1988.

Islam N, Aftabuddin M., Moriwaki A and Hori Y. Immunocytochemical distribution of gamma isoform of protein kinase C (PKC-gamma) following incomplete ischemia. Indian J. Physiol. Pharmacol., 39, 37, 1995.

Kharlamov A., Guidoti A., Costa E., Hayes R. and Armstrong D. Semisynthetic sphingolipids prevent protein kinase C translocation and neuronal damage in the perifocal area following a photochemically induced trombotic brain cortical lesion. J. Neurosci., 13, 2483, 1993.

Koh J. Y., Palmer E. and Cotman C. W. Activation of metabotropic glutamate receptors attenuates N-methyl-D-aspartate neurotoxicity in cortical cultures. PNAS USA, 88, 9431, 1991.

Kurino M., Fukunaga K., Ushio Y. and Miyamoto E. Activation of mitogen-activated protein kinase in cultured rat hippocampal neurons by stimulation of glutamate receptors. J. Neurochem., 65, 1282, 1995.

Lin W. W., Wang C. W. and Chuang D. M. Effects of depolarization and NMDA antagonists on the role of survival of cerebrellar granule cells: a pivotal role for protein kinase C isoforms. J. Neurochem., 68, 2577, 1997.

Mattson M. P. Evidence for the involvement of protein kinase C in neurodegenerative changes in cultured human cortical neurons. Exp. Neurol., 112, 95, 1991.

Miettinen S., Roivainen R., Hokfelt T. and Koistinahol J. Specific induction of protein kinase C-delta subspecies after transient middle cerebral artery occlusion in the rat brain: inhibition by MK-801. J. Neurosci., 16, 6236, 1996.

Nares M., Kuluz J., Neary J., Kang Y., Xu E. and Schleien C. L. Mitogen-activated protein (MAP) kinase activity during and after transient focal cerebral ischemia in rats. Soc. Neurosci. Abs., 24 Pt. 1),223, 1998.

Newell D. W., Barth A., Papermaster V. and Malouf A. T. Glutamate and non-glutamate receptor mediated toxicity caused by oxygen and glucose deprivation in organotypic hippocampal cultures. J. Neurosci., 15, 7702, 1995.

Newton A. C. Protein kinase C: structure, function and regulation. J. Biol. Chem., 270, 28495, 1995.

Roisin M. P., Leinekugel X. and Tremblay E. Implication of protein kinase C in mechanisms of potassium-induced long-term potentiation in rat hippocampal slices. Brain Res., 745, 222, 1997.

Runden E., Seglen P. O., Haug F. -M., Ottersen O. P., Wieloch T., Shamloo M. and Laake J. H. Regional selective neuronal degeneration after protein phosphatase inhibition in hippocampal slice cultures: evidence for a MAP kinase-dependent mechanism. J. Neurosci., 18, 7296, 1998.

Sakai N., Sasaki K., Ikegaki N., Shirai Y., Ono Y. and Saito N. Direct visualization of the translocation of the gamma-PKC in living cells using fusion proteins with green fluorescent protein. J. Cell. Biol., 139, 1465, 1997.

Sato N., Kamino K., Tateishi K., Satoh T., Nishiwaki Y., Yoshiwa A., Miki T. and Ogihara T. Elevated amyloid beta protein (1–40) level induces CREB phosphorylation at serine 133 via p44/42 MAP kinase (Erk1/2)-dependent pathway in rat pheochromocytoma PC12 cells. Biochem. Piophys. Res. Com., 232, 637, 1997.

Stoppini L., Buchs P. A. and Muller D. A simple method for organotypic cultures of nervous tissue. J. Neurosci. Meth., 37, 173, 1991.

Tong L., Toliver-Kinsky T., Taglialatela G., Werrbach-Perez K., Wood T. and Perez-Polo R. Signal transduction in neuronal death. J. Neurochem., 71, 447, 1998.

Vornov J. J., Tasker, R. C. and Coyle T. J. Delayed protection by MK-801 and tetrodotoxin in a rat organotypic hippocampal culture model of ischemia. Stroke, 25, 457, 1994.

Xia Z., Dickens M., Raingeaud J., Davis R. J. and Greenberg M. E. Opposing effects of ERK and JNK-p38 MAP kinases on apoptosis. Science, 270, 1326, 1995.

Xia Z., Dudek H., Miranti C. K. and Greenberg M. E. Calcium influx via the NMDA receptor induces immediate early gene transcription by a MAP kinase/ERK-dependent mechanism. J. Neurosci., 16, 5425, 1996.

Zablocka B and Domanska-Janik K. Involvement of protein kinase C in various cellular systems transducting ischemia evoked signal. Acta Neurobiol. Exp., 53, 25, 1993.

What is claimed is:

1. A method of treatment to achieve neuroprotection of cells in the central nervous system comprising the steps of:
    (a) supplying at least one bioflavonoid in a suitable pharmacological composition; and (b) administering a therapeutically effective dose of the bioflavonoid to achieve protection of neurons from deterioration and cell death.

2. The method of claim 1, further comprising the steps of:
(a) supplying PD098059 in a pharmacologically acceptable carrier; and
(b) administering the PD098059 to obtain a blood plasma concentration of between about 30 μM to about 90 μM.

3. The method of claim 1, further comprising the steps of:
(a) supplying apigenin in a pharmacologically acceptable carrier; and
(b) administering the apigenin to obtain a blood plasma concentration of between about 25 μM and about 100 μM.

4. The method of claim 1, further comprising the step of supplying a bioflavonoid selected from the group consisting of apigetrin, apiin, pelargidenon, versulin, cossmetiin, apioside, cosmosiin, cosmosiine cosmosioside, baicalin, cirsimaritin, 6-hydroxyluteolin, luteoloin, plantaginin, rhoifolin, sorbavin, afrelin, hyperin, isoquercitrin, isorhamnetin, kaempferitrin, kaempferol-7-glucoside, oxyayanin-A, quercetin, quercitrin, rhamnetin and rutin, and their pharmaceutically acceptable salts.

5. The method of claim 1, further comprising the step of administering the bioflavonoid orally.

6. The method of claim 1, further comprising the step of administering the bioflavonoid intravenously.

7. The method of claim 1, further comprising the step of administering the bioflavonoid intramuscularly.

8. The method of claim 1, further comprising the step of administering the bioflavonoid transdermally.

9. The method of claim 1, further comprising the step of administering the bioflavonoid subcutaneously.

10. The method of claim 1, further comprising the step of administering the bioflavonoid by a controlled release vehicle.

11. The method of claim 1, further comprising the step of administering the bioflavonoid in an ophtalmic preparation.

* * * * *